(12) United States Patent
Dwivedi (10) Patent No.: US 11,037,338 B2
(45) Date of Patent: Jun. 15, 2021

(54) RECONSTRUCTING IMAGE DATA

(71) Applicant: Nvidia Corporation, Santa Clara, CA (US)

(72) Inventor: Shekhar Dwivedi, Santa Clara, CA (US)

(73) Assignee: Nvidia Corporation, Santa Clara, CA (US)

( * ) Notice: Subject to any disclaimer, the term of this patent is extended or adjusted under 35 U.S.C. 154(b) by 111 days.

(21) Appl. No.: 16/376,449

(22) Filed: Apr. 5, 2019

(65) Prior Publication Data

US 2020/0066006 A1 Feb. 27, 2020

Related U.S. Application Data

(60) Provisional application No. 62/721,517, filed on Aug. 22, 2018.

(51) Int. Cl.
| | |
|---|---|
| *G06T 11/00* | (2006.01) |
| *G16H 30/40* | (2018.01) |
| *G06T 7/00* | (2017.01) |
| *G06N 20/00* | (2019.01) |

(52) U.S. Cl.
CPC ............ *G06T 11/005* (2013.01); *G06N 20/00* (2019.01); *G06T 7/0012* (2013.01); *G16H 30/40* (2018.01); *G06T 2207/20081* (2013.01); *G06T 2211/424* (2013.01)

(58) Field of Classification Search
CPC ... G06T 7/0012; G06T 11/003; G06T 11/005; G06T 11/006; G06T 2211/412; G06T 2211/421; G06T 2211/424; G06T 2211/428; G06T 2207/20081; G16H 30/40; G06N 20/00; G06N 20/20; G06N 5/003; G06N 3/08
See application file for complete search history.

(56) References Cited

U.S. PATENT DOCUMENTS

| | | | | |
|---|---|---|---|---|
| 2003/0206609 | A1* | 11/2003 | Kling | .................. G06T 11/006 378/4 |
| 2013/0101190 | A1* | 4/2013 | Shi | ...................... G06T 11/006 382/131 |
| 2017/0053423 | A1* | 2/2017 | Ahn | ..................... A61B 6/037 |
| 2017/0206680 | A1* | 7/2017 | Tung | ................. G06F 3/04842 |
| 2018/0061045 | A1* | 3/2018 | Profio | .................... A61B 8/00 |

\* cited by examiner

*Primary Examiner* — Nay A Maung
*Assistant Examiner* — Jose M Torres
(74) *Attorney, Agent, or Firm* — Hogan Lovells US LLP (57) ABSTRACT

This disclosure introduces an approach that includes techniques for determining an optimal weighted execution sequence of available reconstruction algorithms using a multi-processor unit. The introduced approach includes executing a series of optimal weighted execution sequence candidates on a representative slice of the image data and comparing their results to select one of the candidates as the optimal weighted execution sequence.

27 Claims, 4 Drawing Sheets

RECONSTRUCTING IMAGE DATA

CROSS-REFERENCE TO RELATED APPLICATION

This application claims the benefit of U.S. Provisional Application Ser. No. 62/721,517, filed by Shekhar Dwivedi on Aug. 22, 2018, entitled "Algorithm Weighting System for Image Reconstruction," commonly assigned with this application and incorporated herein by reference.

TECHNICAL FIELD

This application is directed, in general, to data imaging. More specifically, the application is directed to a system and method for weighting and sequencing reconstruction algorithms for image reconstruction.

BACKGROUND

Data imaging is an important technology utilized by a wide variety of industries. Depending on the field, the custom of any particular industry in imaging operations may be to produce one or more multi-dimensional images using one or more imaging modalities. In medical imaging, for example, the images can be produced using a host of modalities including: X-ray, MRI, CT scans, and ultrasound. X-ray-based imaging is also used in the security, and oil and gas industries.

SUMMARY

In one aspect, a system for reconstructing image data is described. The system includes: a multi-processor unit configured to receive a request to visualize image data; select reconstruction algorithms to be executed on the image data based on the request; and determine an optimal weighted execution sequence of the reconstruction algorithms. The optimal weighted execution sequence includes a weight for each of the reconstruction algorithms and an execution sequence for the reconstruction algorithms.

In another aspect, a method for reconstructing image data is described. The method includes: receiving a request to visualize image data; selecting reconstruction algorithms to be executed to visualize the image data based on the request; and determining an optimal weighted execution sequence of the reconstruction algorithms, wherein the optimal weighted execution sequence includes a weight for each of the reconstruction algorithms and an execution sequence for the reconstruction algorithms.

BRIEF DESCRIPTION

Reference is now made to the following descriptions taken in conjunction with the accompanying drawings, in which.

DETAILED DESCRIPTION

Image reconstruction is a technique that generates images from data coming from imaging devices, e.g., sensors. Many different reconstruction algorithms exist in literature and practice, and each algorithm provides different benefits to the quality of the end image. The sequencing and weighting of these reconstruction algorithms can have substantial impact on the final image quality, and a unique "recipe" of algorithm sequence and weights may be necessary to produce an optimal image.

Weighting and sequencing are highly dependent on the problem at hand, the application, and several other factors. Testing every combination with different weights and sequences therefore is virtually impossible. As such, image reconstruction has been performed traditionally either by using just one algorithm, usually applied over several—sometimes hundreds—of iterations over the same image data, or by applying a different algorithm during the pre- or post-processing stage(s) than the algorithm used during reconstruction to enhance the end image quality.

However, the number of iterations that an algorithm is applied during the reconstruction is often static regardless of the specific task or dataset reconstruction is being performed for/on. It is often the case that the number of applied iterations well-exceeds the point of diminishing returns, i.e. the point at which the benefit of each additional iteration no longer outweighs the cost of applying the iteration. Moreover, applying different algorithms during pre- or post-processing requires extending the pre- and post-processing time, which is often difficult to accommodate given the lack of time and computing resources. As such, conventional approaches have resulted in marginal or imperceptible benefit while suffering from significantly diminishing returns.

This disclosure introduces a technique that generates an optimal weighted execution sequence of available reconstruction algorithms using a multi-processor unit. The introduced techniques can be parameterized to generate a weighted sequence that provides the best reconstructed image given time and computing resource. It is understood that the "optimal weighted execution sequence" indicates an execution sequence of weighted reconstruction algorithms, according to which a processing unit executes certain reconstruction algorithms on a given image data to reconstruct an image therefrom that exceeds one or more quality preference benchmarks/thresholds under a given time constraint. The optimal weighted execution sequence includes a sequence/order in which reconstruction algorithms should run and respective weights (or iterations, or a percentage of time) with which each reconstruction algorithm should run to reconstruct the image data.

In one embodiment, an introduced technique dynamically determines the optimal weighted sequence for two or more algorithms by testing out multiple weighted sequences during reconstruction and choosing the best sequence. Instead of testing the weighted sequences on the entirety of the image data, the introduced technique tests the weighted sequences on a representative portion from the image data. The introduced technique tests multiple weighted sequences in parallel using the parallel processing capability of the multi-processor unit. As such, the introduced technique can test multiple weighted sequences using significantly smaller amounts of time and computing resources compared to the conventional methods by leveraging parallel processing capabilities of advanced hardware processors (such as one or more GPUs). The introduced technique can also significantly reduce the time and computing resources spent because less pre- and post-processing would be necessary. Furthermore, as the weighted sequence determination process can be separated from the actual reconstruction, the introduced technique can provide the weighted sequence to the user before the reconstruction for further modification if desired.

Figure 1:
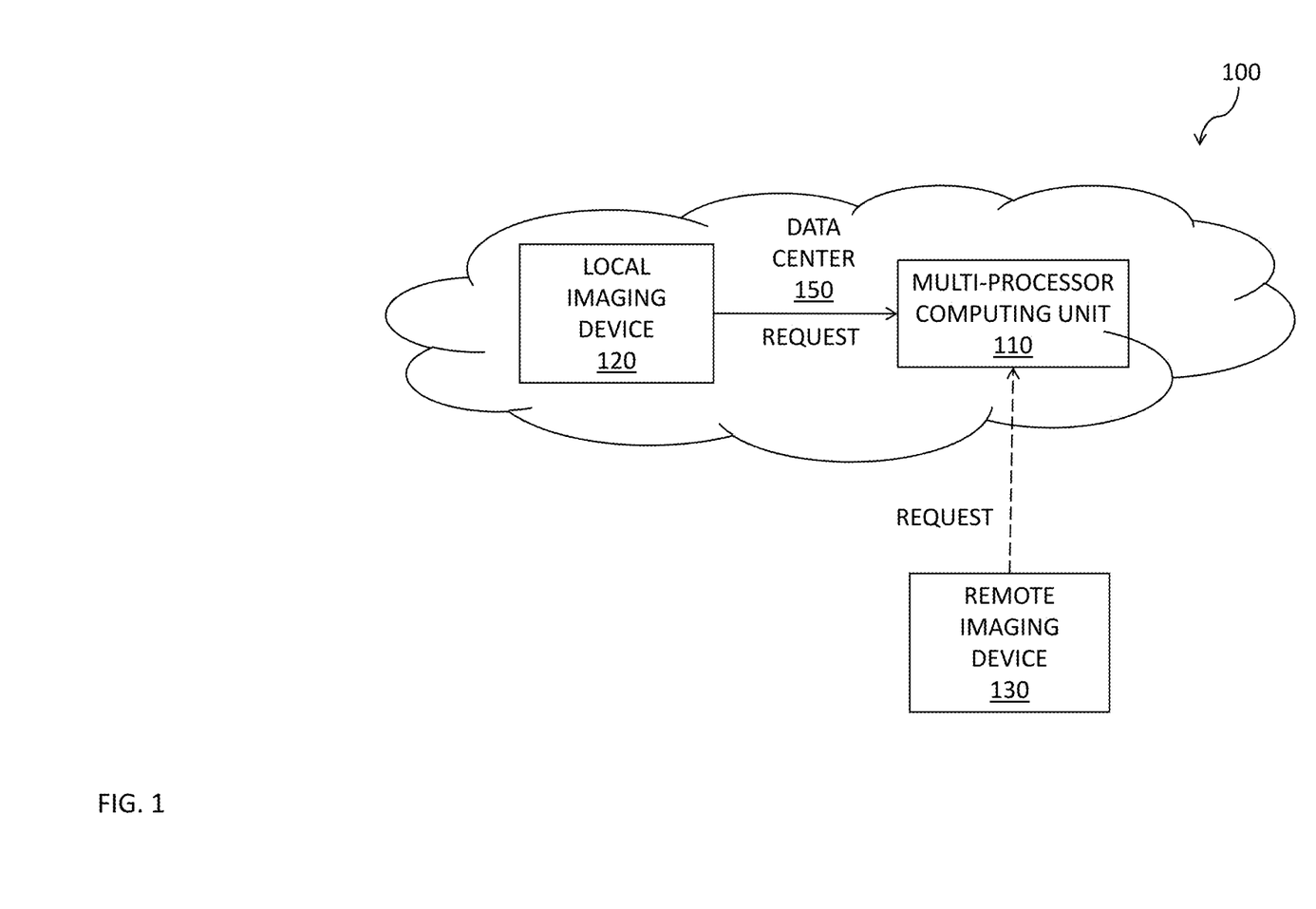
FIG. 1 illustrates an embodiment of a system for reconstructing image data constructed according to the principles of the disclosure.

FIG. 1 illustrates an embodiment of a system 100 for visualizing image data constructed according to the principles of the disclosure. In the illustrated embodiment, the system 100 includes a multi-processor unit 110, a local imaging/computing device 120 and a remote imaging/computing device 130. The multi-processor unit 110 may be co-located with the local device 120 in a datacenter or server 150 for local computing, or located remotely from the remote imaging/computing device 130 for cloud computing. The multi-processor unit 110 may be communicatively connected to the devices 120, 130 over a local area network, a wide area network, a data bus and/or a wireless data protocol based on the locations of the devices 120, 130.

In the illustrated embodiment, the multi-processor unit 110 is configured to determine an optimal weighted execution sequence of reconstruction algorithms for processing image data from one or more of the devices, such as 120 and 130. The multi-processor unit 110 may be any processing unit that is capable of parallel-processing, such as a graphics processing unit (GPU), a central processing unit (CPU), or a combination of both CPU and GPU.

In the illustrated embodiment, each of the devices 120, 130 may be an imaging device that is configured to generate an image data of objects, e.g., organs of a patient. The devices 120, 130 may be a radiography imaging device, a magnetic resonance imaging (MRI) device, nuclear medicine imaging device, ultrasound imaging device, sonography imaging device, elastography imaging device, photoacoustic imaging device, tomography imaging device, echocardiography imaging device, functional near-infrared spectroscopy imaging device, and magnetic particle imaging device. Each of the devices 120, 130 may also be a computing device that is configured to make a request to a connected multi-processor unit, e.g., 110, to determine the optimal weighted execution sequence and to optimally visualize the image data using the optimal weighted execution sequence.

Figure 2:
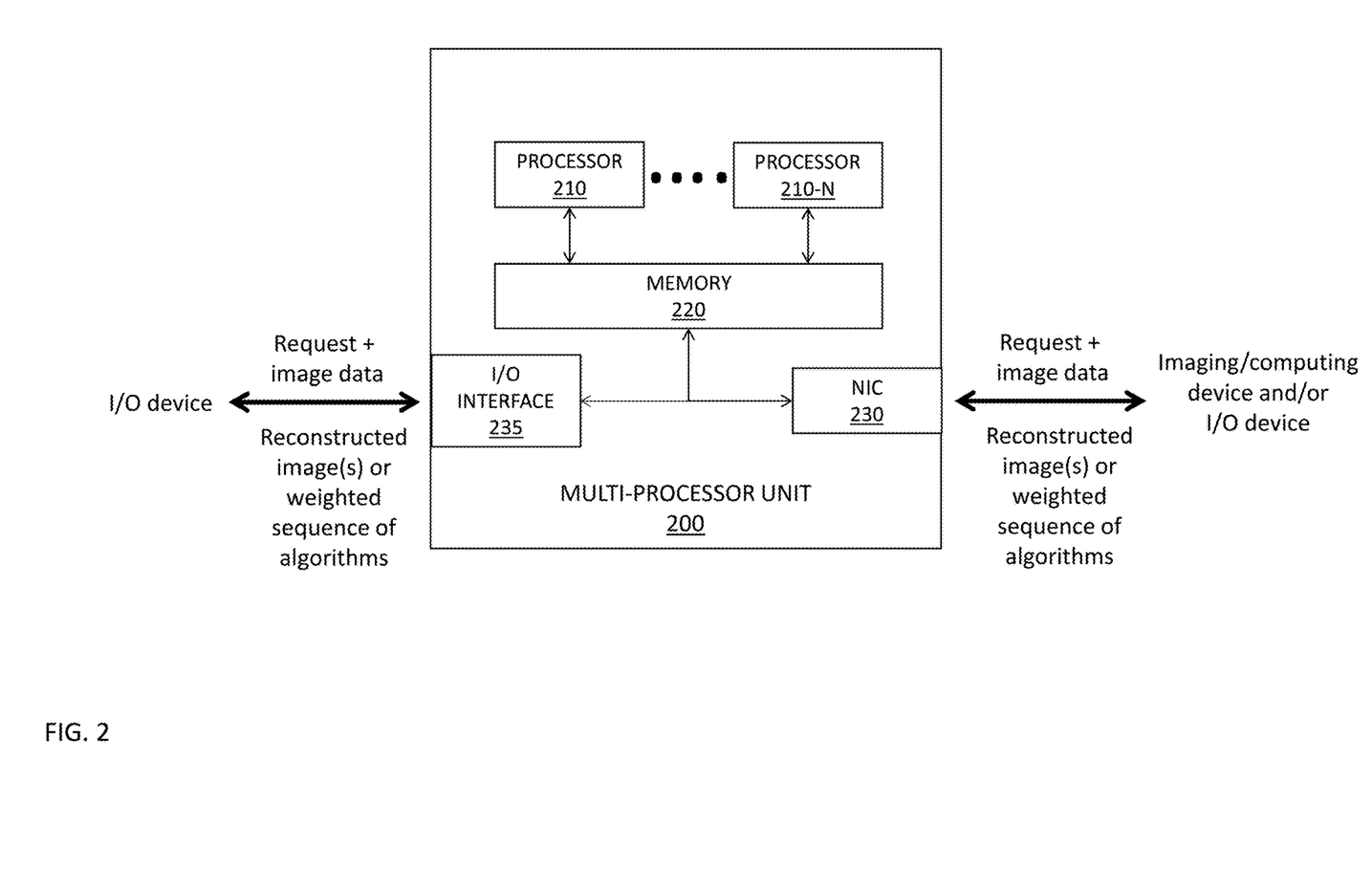
FIG. 2 illustrates an embodiment of a multi-processor unit that is constructed according to the principles of the disclosure.

FIG. 2 illustrates an embodiment of a multi-processor unit 200, such as 110 in FIG. 1, that is constructed according to the principles of the disclosure. The multi-processor 200 includes a plurality of processors 210s, a memory 220, a network interface card (NIC) 230, and an input/output (I/O) interface 235 that are inter-connected to one another using conventional means.

In the illustrated embodiment, the NIC 230 and the I/O interface 235 are configured to receive a request to visualize image data. The request may be received from any communicatively connected computing/imaging device, such as 120, 130 in FIG. 1, or from a directly connected input device, such as (without limitation) a keyboard, a mouse or touch screen. The request may include the image data to be visualized; the reconstruction algorithms to be executed to process the image data; and one or more preferred processing parameters of the requestor.

The NIC 230 and the I/O interfaces 235 are also configured to receive the processing results from the memory 220 and transmit them to an output device, such as (without limitation) a monitor or a display, or to other computing device. The processing results may include visualized images, and/or a weighted sequence of the selected reconstruction algorithms.

In the illustrated embodiment, the memory 220 is a non-transitory medium that is configured to store various data. The memory 220 may store the received requests and inputs, and the processing results of the requests and inputs. The memory 220 may also store a series of instructions that when executed, configures the processors 210s to perform a method for processing image data, an embodiment of which is described below with FIG. 3.

The processors 210s are configured to select reconstructions algorithms to be executed in the optimal weighted execution sequence. Using all available algorithms for sequencing can increase the workload and may not be desirable for all applications and incoming datasets. A directed or curated selection of algorithms for sequencing is essential. The selection of the reconstruction algorithms may be specified in the request or in the inputs from the user. When the algorithms are not specified, the processor 210s may select them from the available reconstruction algorithms based on factors such as: characteristics of the image data, e.g., a modality to which the image data relates and a resolution of the image data; characteristics of available reconstruction algorithms, e.g., processing parameters that the algorithms enhance/reduce, iteration times of the algorithms, points of diminishing return for the algorithms (how effective each reconstruction algorithm is when it is iterated a certain number of times), and coverages, e.g., local or global, of the algorithms (whether a given algorithm only affects a certain region of the image or affects the whole image); characteristics of the patient, e.g., disease/organ being treated and treatment history of the patient; and the preferred processing parameters. It is understood that the listed factors are not exclusive and may include other factors that are related or derivable from the listed factors.

In one embodiment, the selection of the reconstruction algorithms may be performed using a machine learning model. A regression or classification algorithm can be designed. All available algorithms serve as a label set. Ground truth is created by determining the figure of merit for each training set using each algorithm, and then all algorithms that create the figure of merit above/below a certain threshold are considered to be usable for the training set. A feature set may be extracted from image data characteristics, patient/data characteristics, figure of merit characteristics, and time and computing constraints. For any new incoming data, features are extracted, and the machine learning model is evaluated for each available algorithm to come up with an optimum set of algorithms for the new data.

Similar to the reconstruction algorithms, the preferred processing parameters may be specified in the request. The preferred processing parameters refer to parameters that the requestor wants to emphasize during the reconstruction. The preferred processing parameters may include at least one of a preferred performance parameter, such as a preferred amount of time or computing resource for reconstruction, or a preferred visual parameter, such as Signal to Noise ratio (SNR), Organ contrast, Image sharpness at boundaries, Peak SNR, SSIM (Structural similarity index), or SUV (Standard Uptake value) in a functional imaging, e.g., SPECT and PET imaging). It is understood that the listed parameters are not exclusive and may include other parameters that are related or derivable from the listed parameters.

The processors 210s are further configured to determine an optimal weighted execution sequence of the selected reconstruction algorithms. The optimal weighted execution sequence includes a weight for each of the selected reconstruction algorithms and an execution order for the selected reconstruction algorithms.

In one embodiment, the processors 210s determine the optimal weighted execution sequence using the representative slice technique. Using the slice technique, the processor 210s first selects a representative portion of the image data, e.g., a slice that contains the most information about an organ or region of interest. The portion may be selected based on the patient characteristics, such as (without limitation) the disease/condition being treated, the organ(s) being treated, and the treatment history of the patient. For example, for image data pertaining to a lung cancer patient, a portion, e.g., one or more slices, of the image data that is centered on and hence contains the most information about the lung would be selected.

The processors 210s then determine a plurality of weighted execution sequences for the representative slice. The weighted execution sequences represent candidates for the optimal weighted execution sequence. The weighted execution sequences are determined based on various factors such as (without limitation) the preferred processing parameter, the characteristics of the selected reconstruction algorithms, the characteristics of the image data, and the time and computing constraints. The time and computing constraints represent the resources available to complete the request, computation time requirement, and available processing power. It is understood that the listed constraints are not exclusive and may include other constraints that are related or derivable from the listed constraints.

When the weighted execution sequences are determined, the selected algorithms are executed on the representative data according to the weighted execution sequences. The weighted execution sequences are executed in parallel using the multiple processors 210s of the multi-processor unit 200 for maximum efficiency and speed. Each of the weighted execution sequences may be executed on a different processor 210 of the multi-processor unit 200, or the weighted execution sequences may be executed one at a time using all the multiple processors 210s.

Based on the comparison of the reconstructed images, one of the weighted sequences that provides the best figure of merit (FOM) for the preferred processing parameter is selected as the optimal weighted execution sequence. The FOMs of the weighted execution sequences may be compared using mechanisms such as (without limitation): Manual/automatic ROI detection, which either manually or automatically detects a region of interest in the reconstructed images and compares certain processing parameters/values in the regions; Model based evaluation, which uses a predefined model for evaluating a certain region of the reconstructed images; and Multiple user based voting mechanism, in which multiple users vote on which is the best reconstructed image.

In one embodiment, the optimal weighted execution sequence may be determined using a predetermined template. The predetermined template is a fixed template that has been tailored for determining an optimal weighted execution sequence for certain data image and certain patient characteristics. For example, there may be a predetermined template for image data of a certain resolution corresponding to a certain modality and certain disease/condition. The predetermined template may be a transfer function generated from prior reconstruction results.

In another embodiment, the optimal weighted execution sequence may be determined using a machine learning model. Considering the optimal weighted execution sequence for a given application as a label set, a machine learning algorithm (such as Classification, decision tree/random forest, a neural network among many others) can be designed to compute the "best" weighted sequence for a given input dataset. Parameters for the learning algorithm may be extracted from the application at hand, such as (without limitation) the image data characteristics, patient/object characteristics, time and computing constraints, characteristics of the algorithms involved, and figure of merit characteristics. Ground truth is generated by labeling each training set with the optimal weighted sequence from the list of available weighted sequences. Ground truth is generated by an expert after examining a figure of merit for each training set on all weighted sequences from the label set. The machine learning model such as (without limitation) an artificial neural network and/or a regression model can be used.

Once the optimal weighted execution sequence is determined, the processors 210 may execute the selected reconstruction algorithms according to the optimal weighted sequence. Each of the selected reconstruction algorithms is executed on the image data iteratively based on the respective weight, and also sequentially based on the execution order.

Instead of being executed locally, the optimal weighted sequence can also be exported to a different computing system. The optimal weighted sequence may first be stored in the memory 220 and then transmitted to another computing system via the NIC 230.

Figure 3:
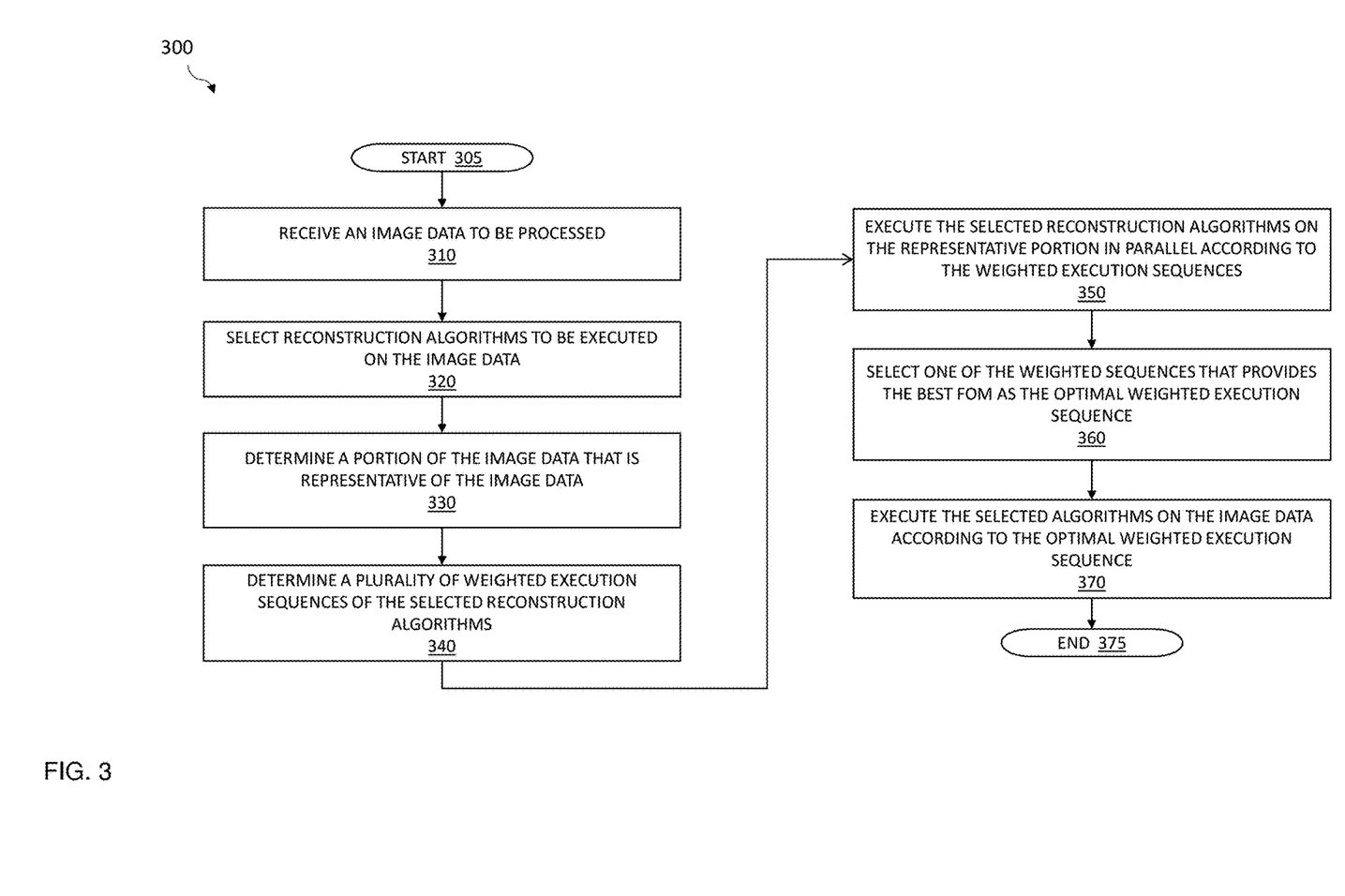
FIG. 3 illustrates a flow diagram of an embodiment of a method for reconstructing image data carried out according to the principles of the disclosure.

FIG. 3 illustrates a flow diagram of an embodiment of a method 300 for visualizing image data carried out according to the principles of the disclosure. The method 300 may be performed by a multi-processor unit such as 200 in FIG. 2. The method 300 starts at step 305.

At step 310, a request to optimally process image data or to determine an optimal weighted execution sequence is received. The request may be received from a local or remote device, such as 120 and 130 in FIG. 1, or from an input device, such as (without limitation) a keyboard, a mouse, or a touch screen that is communicatively connected to the multi-processor unit that is performing the method 300. As discussed above with FIG. 2, the request may include the image data to be processed, the reconstruction algorithms to be executed to process the image data; and one or more preferred processing parameters.

In one example, a request to reconstruct raw sinogram data is received at a multi-processor unit that performs the image reconstruction. The request includes the raw sinogram data and specifies the minimum amount of noise and the maximum organ contrast as the preferred processing parameters. The sinogram data may be received from a remote imaging device via wireless data protocol.

At step 320, reconstruction algorithms to be executed are selected from the available reconstruction algorithms. The request received at step 310 may indicate which reconstruction algorithms are to be executed. Some of the commonly available reconstruction algorithms include: Simultaneous Iterative Reconstruction Technique (SIRT); Simultaneous Algebraic Reconstruction Technique (SART); Conjugate Gradient Least Square (CGLS); Ordered Subset Expectation-Maximization (OSEM), which is an optimized version of MLEM, where a subset of data is used in the iterative process; and Maximum Likelihood Expectation-Maximization (MLEM), which performs computation for each pixel in the image. A non-iterative, analytical algorithm such as (without limitation) Filtered Back Projection (FBP) may be also available for selection.

When the algorithms are not specified, they may be selected based on the factors such as: characteristics of the image data, e.g., a modality to which the image data relates and a resolution of the image data; characteristics of the available reconstruction algorithms, e.g., processing parameters that the algorithms enhance and iteration times of the algorithms; characteristics of the patient, e.g., disease/organ being treated and treatment history of the patient; and the preferred processing parameters. It is understood that the listed factors are not exclusive and may include other factors that are not listed but relatable or derivable from the listed factors.

Continuing with the above example, the request does not specify reconstruction algorithms to be used. As such, considering 1) the patient has a history of lung cancer treatments (characteristics of the patient), 2) the image data is raw sonogram data (characteristics of the image data), and 3) SIRT, SART, and CGLS address SNR and organ contrast (characteristics of the available algorithms), the multi-processor unit selects SART, CGLS, and SIRT for reconstruction.

In steps 330-360, an optimal weighted execution sequence of the selected algorithms is determined. The optimal weighted execution sequence includes a weight for each of the selected reconstruction algorithms and an execution order for the selected reconstruction algorithms. The optimal weighted execution sequence represents a weighted execution sequence that provides the best FOM for the preferred processing parameters under the given time period when each of the selected algorithms is executed based on their respective weight and order of the weighted execution sequence.

At the step 330, a portion of the image data that is representative of the image data (representative slice) is determined. The representative portion may be selected based on the patient characteristics, such as (without limitation) the disease/condition being treated, the organ(s) being treated, and the treatment history of the patient. In the above example, based on the patient characteristics that the patient is a lung cancer patient with a history of lung cancer treatments, a slice of the image data that captures (centered on) the lung is selected as the representative portion.

At step 340, a plurality of weighted execution sequences of the selected reconstruction algorithms are determined. As each the weighted execution sequences represents a candidate for the optimal weighted execution sequence, each weighted execution sequence includes a weight (a number of iterations) and an execution order for each reconstruction algorithm. The weights and sequence for each of the weighted execution sequences are determined based on various factors.

The factors include the preferred processing parameter, the characteristics of the selected reconstruction algorithms, the time and computing constraints, and the characteristics of the image data. The preferred processing parameters may be specified in the request or in the input from the user. As disclosed above, the preferred processing parameters may include at least one of a preferred performance parameter such as a preferred amount of time or computing resource for reconstruction, or a preferred visual parameter such as SNR, Organ contrast, Image sharpness at boundaries, Peak SNR, SSIM, or SUV in a functional imaging. It is understood that the listed parameters are not exclusive and may include other parameters that are not listed but relatable or derivable from the listed parameters.

The characteristics of the selected algorithms represents the algorithms' performance characteristics such as (without limitation) the preferred processing parameters that the algorithms address, iteration times of the algorithms, points of diminishing return for the algorithms, and coverages of the algorithms (whether a given algorithm only affects a certain region of the image or affects the whole image). The time and computing constraints represents the resources available to complete the request, such as (without limitation) available time and processing power. The characteristics of the image data may include a modality to which the image data corresponds, and a resolution of the image data. It is understood that the listed characteristics/constraints are not exclusive and may include other characteristics/constraints that are not listed but relatable or derivable from the listed characteristics/constraints.

Following the above example, the multi-processor unit determines that the selected algorithm can be sequenced in six different sequences; SART→CGLS→SIRT, SART→SIRT→CGLS, CGLS→SART→SIRT, CGLS→SIRT→SART, SIRT→CGLS→SART, SIRT→SART→CGLS. Of the six sequences, the multi-processor chooses three sequences SART→CGLS→SIRT, SART→SIRT→CGLS, CGLS→SART→SIRT based on the coverages of the algorithms and the time and computing constraints. For example, the selected sequences execute SART, which works globally, before SIRT, which works locally.

The multi-processor also determines that four different sets of weights for the selected sequence of SART, CGLS, SIRT, can be used. For example, The first set of weights has respective weights of 100 iterations, 25 iterations, and 75 iterations for SART, CGLS, SIRT; the second one has 95, 20, 85 respective iterations; the third one has 95, 35, 70 respective iterations; and the fourth one has 110, 20, 70 respective iterations. The weights have been selected as above based on the fact that the points of diminishing return for the algorithms are 110, 40, 80 and the time constraint is 200 iterations.

When the weighted execution sequences are determined, the selected algorithms are executed on the representative data in parallel according to the weighted execution sequences at step 350. For maximum efficiency, each sequence may be executed on each different one of the available processors, or the weighted execution sequences may be executed one at a time using all the available processors. Based on the comparison of the reconstructed images, one of the weighted sequences that provides the best figure of merit (FOM) for the preferred processing parameter is selected as the optimal weighted execution sequence at step 360. The FOMs of the weighted execution sequences may be compared using mechanisms such as (without limitation) Manual/automatic ROI detection, Model based evaluation and Multiple user-based voting mechanism.

Continuing with the example, as there are three sequences with four different sets of weights, there are 12 combinations of weighted sequences. The 12 combinations are executed in parallel by four processors of the multi-processor unit in three stages. After execution, using automatic ROI detection that focuses on SNR and organ contrast around the lung, the sequence of SART→CGLS→SIRT with respective weights of 100, 25, 75 iterations has been computed to provide the lowest SNR with the highest organ contrast, and therefore selected as the optimal weighted execution sequence.

It is understood that instead of steps 330-360, the optimal weighted execution sequence can also be determined using a predetermined template, or a machine learning model. The predetermined template may be a fixed template that is best for certain data image and patient characteristics. For example, there may be a predetermined template available for image data of a certain resolution that corresponds to a certain modality and/or certain disease/condition. The predetermined template may be a transfer function generated from prior reconstruction/processing results. It is understood that the predetermined template may be generated during "off-peak" hours, such as during night or weekend, and/or by "offline" servers that are not performing the reconstruction, where more computing resource is available.

For embodiments that employ a machine learning model for deriving optimal weighting and sequencing, the optimal weighted execution sequence for a given application is considered as label set. A machine learning algorithm (such as Classification, decision tree/random forest, a neural network among many others) can be designed to compute the "best" weighted sequence for a given input dataset. Parameters for the learning algorithm may be extracted from application at hand, such as (without limitation) image data characteristics, patient/object characteristics, time and computing constraints, characteristics of the algorithms involved, and figure of merit characteristics. Ground truth is generated by labeling each training set with the optimal weighted sequence from a list of available weighted sequences. Ground truth may be generated by an expert after examining the figures of merit produced for each training set on all weighted sequences from the label set. The machine learning model such as an artificial neural network and/or a regression model can be used.

At step 370, the selected algorithms are executed according to the optimal weighted execution sequence. Each of the selected reconstruction algorithms is executed on the image data iteratively based on the respective weight, and also sequentially based on the execution order. Instead of the step 370, the method 300 may send the optimal weighted sequence to a different computing system for execution. The optimal weighted sequence may first be stored in the memory, such as 220 in FIG. 2, and then transmitted to another computing system using a NIC such as 230 in FIG. 2.

In the example, the request specified for the reconstruction of the image data. As such, the selected algorithms are executed on the entire imaging dataset according the optimal weighted execution sequence and the resulting images are provided to the requestor. If the request specified for the determination of the optimal weighted execution sequence, the selected sequence would be provided to the requestor. The method 300 ends at step 375.

Figure 4:
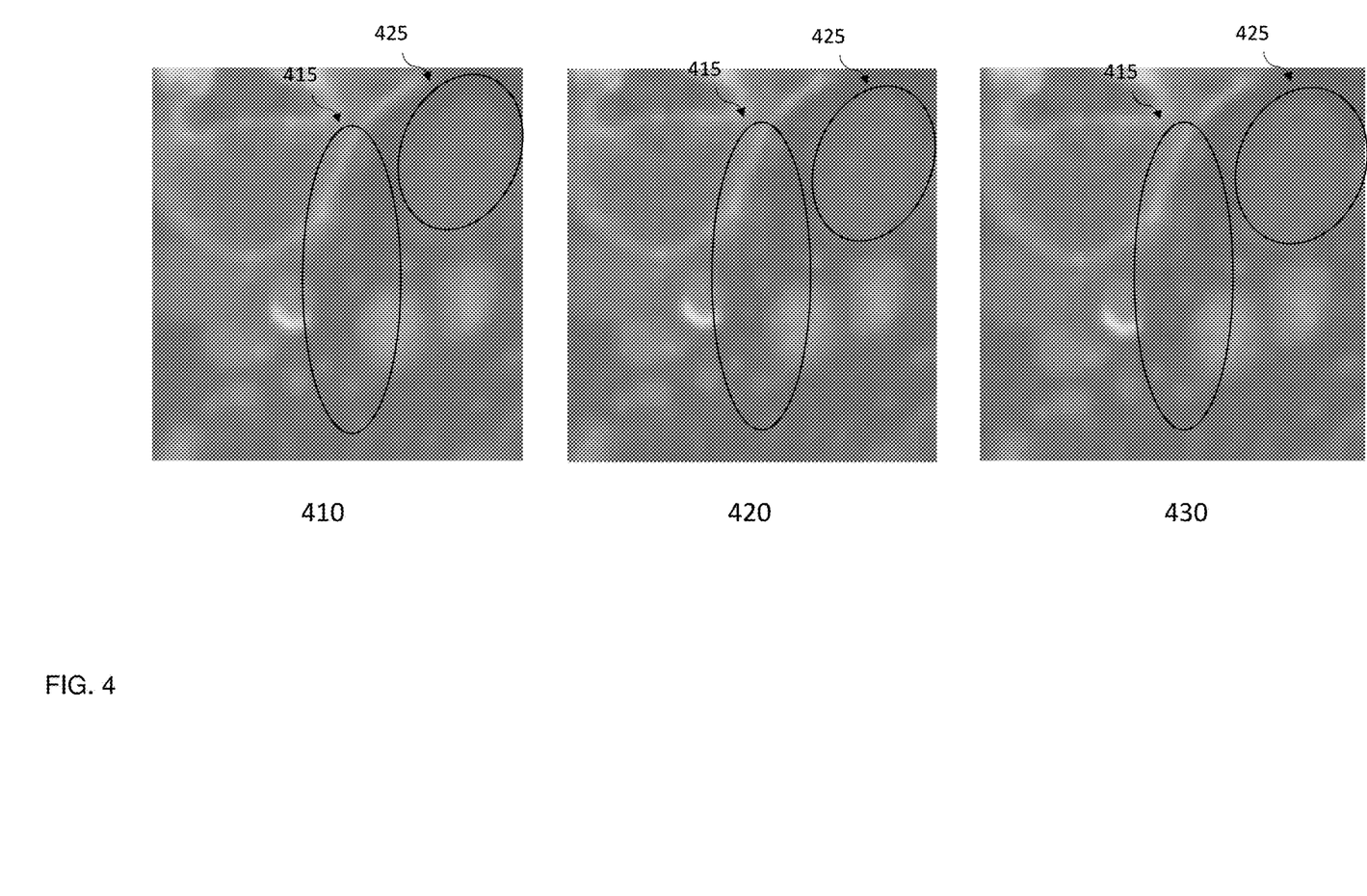
FIG. 4 illustrates examples of reconstructed images.

FIG. 4 depicts three differently reconstructed images 410, 420, 430 of the same image data to show the difference between images reconstructed from using a single reconstruction algorithm and multiple reconstruction algorithms. The image data is reconstructed from an abdominal CT sinogram data. The images 410, 420, 430 show the abdominal area near the backbone and kidneys.

First image 410 depicts an image reconstructed from executing a first algorithm (algorithm A) for 200 iterations. The image is reconstructed in approximately 130 seconds. While the first algorithm may be suitable for removing the background noise, its level of detail of First image 410 is low compared to the second and third images 420, 430. For example, regions 415 and 425 are not clearly marked as the other two images 420, 430. Upon careful examination, it can be observed that certain details within the regions 415 and 425 in the first image 410 are absent.

Second image 420 depicts an image reconstructed from executing a second algorithm (algorithm B) for 200 iterations. The image is reconstructed in approximately. 60 seconds. In this example, the second algorithm may be suitable for retaining the details, but compromises on background noise as the regions 415 and 425 appear noisier than the first and third image 410, 430. Upon careful examination, it can be observed that the regions 415 and 425 provide better internal structural details of very small organs and details.

Third image 430 depicts an image reconstructed from executing the first algorithm for the first 100 iterations and the second algorithm for the next 100 iterations. The third image 430 has retained a relatively high level of detail while removing the background noise to a large extent. Its run time is approximately. 75 seconds. The depicted images illustrate how for even a simple weighted execution sequence, the execution sequence of A→B with 100 iterations for each algorithm (equal weight), can improve the image reconstruction process.

In interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Those skilled in the art to which this application relates will appreciate that other and further additions, deletions, substitutions and modifications may be made to the described embodiments. It is also to be understood that the terminology used herein is for the purpose of describing particular embodiments only, and is not intended to be limiting, since the scope of the present disclosure will be limited only by the claims. Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, a limited number of the exemplary methods and materials are described herein.

It is noted that as used herein and in the appended claims, the singular forms "a", "an", and "the" include plural referents unless the context clearly dictates otherwise.

The above-described apparatuses, systems or methods or at least a portion thereof may be embodied in or performed by various processors, such as digital data processors or computers, wherein the processors are programmed or store executable programs or sequences of software instructions to perform one or more of the steps of the methods or functions of the apparatuses or systems. The software instructions of such programs may represent algorithms and be encoded in machine-executable form on non-transitory digital data storage media, e.g., magnetic or optical disks, random-access memory (RAM), magnetic hard disks, flash memories, and/or read-only memory (ROM), to enable various types of digital data processors or computers to perform one, multiple or all of the steps of one or more of the above-described methods or functions of the system described herein.

Certain embodiments disclosed herein or features thereof may further relate to computer storage products with a non-transitory computer-readable medium that has program code thereon for performing various computer-implemented operations that embody at least part of the apparatuses, the systems, or to carry out or direct at least some of the steps of the methods set forth herein. Non-transitory medium used herein refers to all computer-readable media except for transitory, propagating signals. Examples of non-transitory computer-readable medium include but are not limited to: magnetic media such as hard disks, floppy disks, and magnetic tape; optical media such as CD-ROM disks; magneto-optical media such as floptical disks; and hardware devices that are specially configured to store and execute program code, such as ROM and RAM devices. Examples of program code include both machine code, such as produced by a compiler, and files containing higher level code that may be executed by the computer using an interpreter.

What is claimed is:

1. A system for reconstructing image data, the system comprising:
a multi-processor unit including a plurality of processors, at least one of the processors configured to:
receive a request to process image data;
select one or more reconstruction algorithms to be executed on said image data based on said request; and
determine an optimal weighted execution sequence of said one or more reconstruction algorithms by: determining a representative portion of said image data based at least on patient characteristics; determining a plurality of weighted execution sequences of said reconstruction algorithms; executing said reconstruction algorithms on said representative portion according to said weighted execution sequences in parallel; and selecting one of said weighted execution sequences that provides the best figure of merit (FOM) for a preferred processing parameter as said optimal weighted execution sequence.

2. The system of claim 1, wherein said at least one processor is further configured to execute said reconstruction algorithms according to said optimal weighted execution sequence.

3. The system of claim 1, further comprising an imaging device communicatively coupled to said multi-processor unit and configured to generate said image data and transmit said image data to said multi-processor unit.

4. The system of claim 3, wherein said imaging device is a remote imaging device located remotely from said multi-processor unit.

5. The system of claim 3, wherein said imaging device is a local imaging device co-located with said multi-processor unit in a server.

6. The system of claim 1, wherein said weighted execution sequences are determined based on at least one of: resource constraints; characteristics of said image data; characteristics of said reconstruction algorithms; said preferred processing parameter; or said patient characteristics.

7. The system of claim 6, wherein said preferred processing parameter includes one or more of a preferred performance parameter or a preferred visual parameter.

8. The system of claim 6, wherein said characteristics of said reconstruction algorithms include at least one of: processing parameters said reconstruction algorithms address, iteration times of said reconstruction algorithms, points of diminishing return of said reconstruction algorithms, or coverages of said reconstruction algorithms.

9. The system of claim 6, wherein said characteristics of said image data include at least one of: a modality to which said image data relates, or a resolution of said image data.

10. The system of claim 6, wherein said patient characteristics includes at least one of: a condition or disease being treated, an organ or an area of a human body being treated, or a treatment history of a patient with which said image data is associated.

11. The system of claim 6, wherein said request includes said image data, said preferred processing parameter, and said reconstruction algorithms.

12. The system of claim 1, wherein said optimal weighted execution sequence is determined using a machine learning model.

13. The system of claim 1, wherein said optimal weighted execution sequence includes a weight for each of said reconstruction algorithms and an execution sequence for said one or more reconstruction algorithms.

14. The system of claim 1, wherein each of said weighted execution sequences is executed by a different processor of said multi-processor unit when executed in parallel.

15. A method for processing image data, said method comprising:
receiving a request to process image data;
selecting one or more reconstruction algorithms to be executed to process said image data based on said request; and
determining an optimal weighted execution sequence of said reconstruction algorithms, wherein said determining includes: determining a representative portion of said image data based at least on patient characteristics; determining a plurality of weighted execution sequences of said reconstruction algorithms; executing said reconstruction algorithms on said representative portion according to said weighted execution sequences in parallel; and selecting one of said weighted execution sequences that provides the best figure of merit (FOM) for a preferred processing parameter as said optimal weighted execution sequence.

16. The method of claim 15, further comprising executing said reconstruction algorithms according to said optimal weighted execution sequence.

17. The method of claim 15, wherein said request is received from an imaging device communicatively coupled to a multi-processor unit performing said method.

18. The method of claim 15, wherein said weighted execution sequences are determined based on at least one of: resource constraints; characteristics of said image data; characteristics of said reconstruction algorithms; said preferred processing parameter; or said patient characteristics.

19. The method of claim 18, wherein said preferred processing parameter includes one or more of a preferred performance parameter or a preferred visual parameter.

20. The method of claim 18, wherein said characteristics of said reconstruction algorithms include at least one of: processing parameters of the said reconstruction algorithms address, iteration times of said reconstruction algorithms, points of diminishing return of said reconstruction algorithms, or coverages of said reconstruction algorithms.

21. The method of claim 18, wherein said characteristics of said image data include at least one of: a modality to which said image data relates, or a resolution of said image data.

22. The method of claim 18, wherein said patient characteristics includes at least one of: a condition or disease being treated, an organ or an area of a human body being treated, or a treatment history of a patient with which said image data is associated.

23. The method of claim 18, wherein said request includes said image data, said preferred processing parameter, and said reconstruction algorithms.

24. The method of claim 15, wherein said optimal weighted execution sequence is determined using a machine learning model.

25. The method of claim 15, wherein said optimal weighted execution sequence includes a weight for each of said reconstruction algorithms and an execution sequence for said one or more reconstruction algorithms.

26. The method of claim 25, wherein each of said reconstruction algorithms is executed on said image data iteratively based on said respective weight and sequentially based on said execution sequence.

27. The method of claim 15, wherein said FOM is determined using at least one of: Manual/automatic ROI detection, Model based evaluation, or Multiple user based voting mechanism.

* * * * *